US00PP20055P2

(12) United States Plant Patent
Skotak

(10) Patent No.: US PP20,055 P2
(45) Date of Patent: Jun. 2, 2009

(54) ***GUZMANIA* PLANT NAMED 'DURAPU'**

(50) Latin Name: *Guzmania hybrida*
Varietal Denomination: Durapu

(76) Inventor: Chester Skotak, Apdo. 652, Alajuela (CR), 4050

( * ) Notice: Subject to any disclaimer, the term of this patent is extended or adjusted under 35 U.S.C. 154(b) by 0 days.

(21) Appl. No.: 12/008,012

(22) Filed: Jan. 7, 2008

(51) Int. Cl.
*A01H 5/00* (2006.01)

(52) U.S. Cl. ..... Plt./371
(58) Field of Classification Search ..... Plt./371
See application file for complete search history.

*Primary Examiner*—S. B. McCormick Ewoldt

(57) ABSTRACT

A new and distinct *Guzmania* cultivar named 'Durapau' is disclosed, characterized by large, decorative purple bracts, and a straight, upright peduncle.

1 Drawing Sheet

Figure 1:
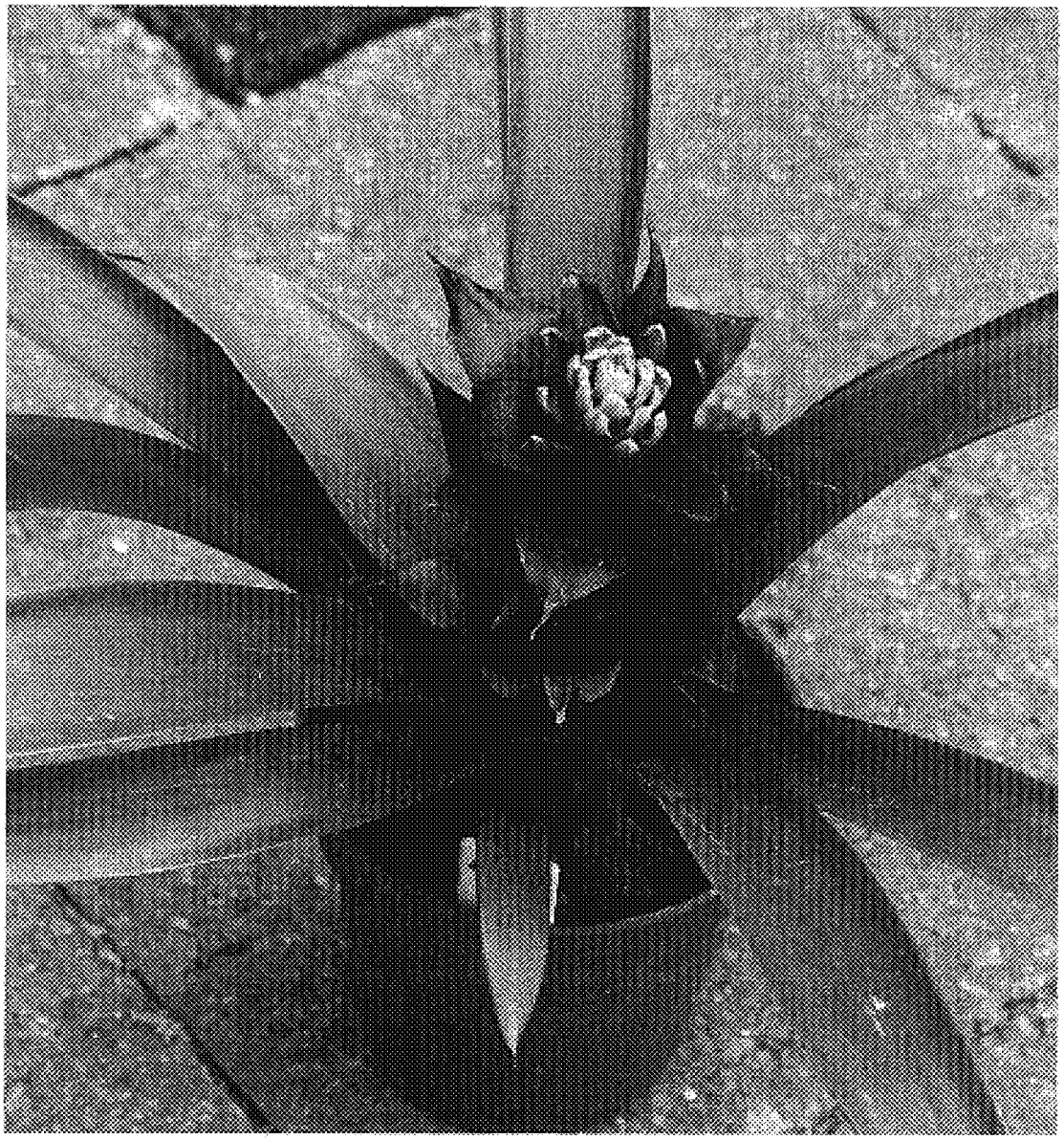

Latin name of the genus and species: *Guzmania hybrida.*
Variety denomination: 'Durapau'.

BACKGROUND OF THE INVENTION

The new cultivar is a product of a planned breeding program. The new variety originated from a cross pollination of an unnamed, unknown seed parent and an unnamed, unknown pollen parent, both *Guzmania hybrida* made by the inventor during 1998.

It was discovered by the inventor, Chester Skotak Jr., a citizen of Costa Rica, in March 2001 in Ajauela, Costa Rica in a group of seedlings resulting from the 1998 crossing.

Asexual reproduction of the new cultivar 'Durapau' was first performed in Costa Rica by tissue culture in April 2003 'Durapau' has been reproduced by micro-propagation and has shown that the unique features of this cultivar are stable and reproduced true to type.

SUMMARY OF THE INVENTION

The cultivar 'Durapau' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Durapau'. These characteristics in combination distinguish 'Durapau' as a new and distinct *Guzmania* cultivar:

1. Foliage resistant to stress.
2. Green foliage.
3. Very straight, dark purple inflorescence.
4. Suitability as an indoor pot plant.
5. Strap shaped leaves occurring in tight, regular whorls.

Plants of the new cultivar 'Durapau' cannot be compared to either seed parent or pollen parent as records of those characteristics were not kept. However, 'Durapau' can be compared to the unpatented commercial variety *Guzmania* 'El Cope.' Plants of 'El Cope' are similar to plants of 'Durapau' in most horticultural characteristics, however, 'El Cope' has a red inflorescence, while 'Durapau' has a purple inflorescence. Additionally, 'Durapau' has a straighter inflorescence than 'El Cope.'

BRIEF DESCRIPTION OF THE PHOTOGRAPH

The accompanying photograph in FIG. 1 illustrates in full color a typical plant of 'Durapau' grown in a greenhouse. This plant is approximately 18 months old, shown in a 13 cm pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Durapau' plants grown in a climate controlled greenhouse in Evergem, the Netherlands. Temperatures ranged from 18° C. to 22° C. at night to 18° C. to 22° C. during the day. No artificial light, photoperiodic treatments or chemical treatments were given to the plants. Measurements and numerical values represent averages of typical plant types.

Botanical classification: *Guzmania hybrida* cultivar 'Durapau.'

PLANT

Growth habit: Upright, forming compact rosettes around a single axis. One straight, upright inflorescence arising from the center of plant.
Plant shape: Inverted triangle.
Height: Approximately 14.3 cm.
Plant spread: Approximately 36.6 cm in a 13 cm pot.
Normal pot size: 13, 15, 18 cm.
Growth rate: Slow.
Branching characteristics: Upright, non-branching.
Number of leaves per stem: Approximately 17.
Age of plant described: Approximately 18 months.

FOLIAGE

Leaf:
*Arrangement.*—Whorled.
*Average leaves per plant.*—17 per rosette.
*Average length.*—Approximately 20.6 cm.

*Average width.*—Approximately 2.7 cm.
*Shape of blade.*—Oblanceolate.
*Aspect.*—Slightly recurved.
*Apex.*—Sharply acute.
*Base.*—Decurrent.
*Margin.*—Entire.
*Texture of top surface.*—Smooth, moderately glossy.
*Texture of bottom surface.*—Smooth, moderately glossy.
*Color.*—Young foliage upper side. Near R.H.S. Green to yellow-green; in between 137A and 147A, base flushed brown; 200B/C Young foliage under side: Near R.H.S. Yellow-green 146A, base greyed-purple; 187A. Mature foliage upper side: Near R.H.S. Yellow-green; 147A, margins at the base flushed greyed-purple; 187A. Mature foliage under side: Near R.H.S. Yellow-green; 146A, darker towards the base; 147A and slightly flushed greyed-purple; 187A.
*Venation.*—Type: Parallel. Venation coloration: Identical/Indistinguishable from foliage.

Petiole: Not present, sessile.

INFLORESCENCE

General description: Simple spike (scape) consisting of many bracts only. No individual flowers are visible. Spike emerges from the centre of the rosette. Inflorescence is formed by conspicuous bracts.
*Inflorescence longevity.*—Approximately 10 weeks.
*Inflorescence height.*—12.9 cm.
*Inflorescence width.*—7.4 cm.

Peduncle:
*Length.*—6.2 cm.
*Width.*—0.7 cm.
*Aspect.*—Very straight, 90° angle to rosette.
*Strength.*—Very strong.
*Color.*—Near RHS. White 157A.

Bracts:
*Average number of bracts.*—75 Terminal bracts and 30 Scape Bracts.
*Shape.*—Ligulate.
*Length.*—5.7 cm.
*Width.*—3.2 cm.
*Tip.*—Acute.
*Base.*—Sheathed.
*Margin.*—Entire.
*Color upperside.*—Near RHS Greyed-Purple N186C and 187A.
*Color underside.*—Near RHS Greyed-Purple 187A.
*Coloration scape bracts.*—Both sides Near RHS Greyed-Purple 187B, with a lighter base of 187C/D.

OTHER CHARACTERISTICS

Reproductive organs: Not Present.
Disease resistance: Neither resistance nor susceptibility to diseases or pests has been observed in this variety.
Drought tolerance and cold tolerance: Observed to tolerate temperatures to 40° C. without any negative effects. Temperature tolerance above this range has not been observed. Tolerance of cold temperatures has not been observed.
Fruit/seed production: Not observed.

What is claimed is:

1. A new and distinct cultivar of *Guzmania* plant named 'Durapau' as herein illustrated and described.

* * * * *

UNITED STATES PATENT AND TRADEMARK OFFICE

CERTIFICATE OF CORRECTION

PATENT NO. : PP 20,055 P2
APPLICATION NO. : 12/008012
DATED : June 2, 2009
INVENTOR(S) : Chester Skotak It is certified that error appears in the above-identified patent and that said Letters Patent is hereby corrected as shown below:

On the title page item (54), “Durapu” should read --Durapau--

On the title page item (50), line 2, “Durapu” should read --Durapau--

Signed and Sealed this

Fourth Day of August, 2009

John Doll

JOHN DOLL
*Acting Director of the United States Patent and Trademark Office*